United States Patent [19]

Rentzea et al.

[11] 4,368,066
[45] Jan. 11, 1983

[54] 1,3-DIOXAN-5-YL-ALKENYLTRIAZOLES, THEIR PREPARATION, THEIR USES IN REGULATING PLANT GROWTH, AND REGULATORS CONTAINING THESE COMPOUNDS

[75] Inventors: Costin Rentzea, Heidelberg; Karl-Heinz Feuerherd; Bernd Zeeh, both of Ludwigshafen; Johann Jung, Limburgerhof, all of Fed. Rep. of Germany

[73] Assignee: BASF Aktiengesellschaft, Fed. Rep. of Germany

[21] Appl. No.: 279,585

[22] Filed: Jul. 1, 1981

[30] Foreign Application Priority Data

Jul. 10, 1980 [DE] Fed. Rep. of Germany ....... 3026140

[51] Int. Cl.³ .................. A01N 43/64; C07D 405/06; C07D 409/06
[52] U.S. Cl. .......................................... 71/76; 71/78; 71/90; 71/92; 542/432; 542/457; 542/458; 542/466; 548/262; 549/372
[58] Field of Search ............... 542/457, 458, 432, 466; 71/76, 78, 90, 92

[56] References Cited

U.S. PATENT DOCUMENTS 3,156,554 11/1964 Tolbert ................................. 71/2.7

FOREIGN PATENT DOCUMENTS 2739352 3/1979 Fed. Rep. of Germany ...... 548/262

Primary Examiner—Alton D. Rollins
Attorney, Agent, or Firm—Keil & Witherspoon

[57] ABSTRACT

Novel 1,3-dioxan-5-yl-alkenyltriazoles of the formula

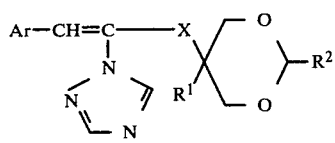

where $R^1$ and $R^2$ are identical or different and each is hydrogen or alkyl of 1 to 5 carbon atoms, Ar is furanyl, thienyl, biphenylyl or naphthyl, or is phenyl which is unsubstituted or substituted by alkyl, alkoxy or alkenyl, each of 1 to 5 carbon atoms, or by fluorine, chlorine, bromine, iodine, nitro, trifluoromethyl or phenoxy, and X is C=O, —CH(OH)— or —CH(O—COR³)—, where $R^3$ is unsubstituted or halogen- or alkoxy-substituted alkyl of 1 to 5 carbon atoms or alkenyl of 2 to 5 carbon atoms or aryl, their salts and metal complexes, and their preparation. The novel compounds are plant growth regulators.

10 Claims, No Drawings

1,3-DIOXAN-5-YL-ALKENYLTRIAZOLES, THEIR PREPARATION, THEIR USES IN REGULATING PLANT GROWTH, AND REGULATORS CONTAINING THESE COMPOUNDS

The present invention relates to novel 1,3-dioxan-5-yl-alkenyltriazoles, to processes for their preparation, to methods for regulating plant growth with these compounds, and to plant-growth regulators containing these compounds.

It is known that 2-chloroethyl-trimethylammonium chloride (chlorocholine chloride, CCC) (cf. U.S. Pat. No. 3,156,554) can be used to influence plant growth. Using this compound it is possible, for example, to inhibit growth in height in some cereals and to inhibit vegetative growth in certain other crop plants. The effect of this compound, especially if low amounts are used, is however not always satisfactory and does not conform to practical requirements.

It is also known to use 3,3-dimethyl-2-(1,2,4-triazol-1-yl)-1-(4-chlorobenzoyl)-butane to influence plant growth (German Laid-Open Application DOS 2,739,352).

We have found that 1,3-dioxan-5-yl-alkenyltriazoles of the formula I

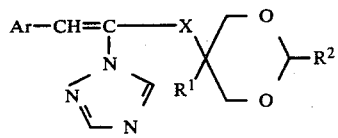

where $R^1$ and $R^2$ are identical or different and each is hydrogen or alkyl of 1 to 5 carbon atoms, Ar is furanyl, thienyl, biphenylyl or naphthyl, or is phenyl which is unsubstituted or substituted by alkyl, alkoxy or alkenyl, each of 1 to 5 carbon atoms, or by fluorine, chlorine, bromine, iodine, nitro, trifluoromethyl or phenoxy, and X is C=O, —CH(OH)— or —CH(O—COR$^3$)—, where $R^3$ is unsubstituted or halogen- or alkoxy-substituted alkyl of 1 to 5 carbon atoms or alkenyl of 2 to 5 carbon atoms or aryl, their salts and metal complexes, are outstandingly suitable for influencing plant growth and are very well tolerated by plants.

The compounds according to the invention can be formed in two geometrical isomer forms, namely Z and E, depending on the configuration of the substituents on the double bond. If X is a chirality center, the compounds of the formula I can additionally exist as enantiomer mixtures or as racemates. Single geometrical isomers and single enantiomers can be obtained, by conventional methods, from the isomer mixtures usually resulting from the process of synthesis. Either the individual geometrical isomers or enantiomers, or the mixtures resulting from their method of synthesis can be used as plant growth regulators, the use of the mixtures being preferred.

$R^1$ and $R^2$ are, for example, hydrogen, methyl, ethyl, n-propyl, isopropyl, n-butyl, sec.-butyl, iso-butyl, tert.-butyl, n-pentyl and neopentyl.

Ar is, for example, furan-2-yl, thien-2-yl, thien-3-yl, 4-biphenyl, naphth-1-yl, naphth-2-yl, phenyl, 4-fluorophenyl, 2-chlorophenyl, 3-chlorophenyl, 4-chlorophenyl, 4-bromophenyl, 2,4-dichlorophenyl, 3,4-dichlorophenyl, 3,5-dichloro-2-methoxyphenyl, 2,3,4-trichlorophenyl, 2-methoxyphenyl, 2,4-dimethoxyphenyl, 3-methoxyphenyl, 4-methoxyphenyl, 4-ethoxyphenyl, 4-tert.-butoxyphenyl, 4-methylphenyl, 4-ethylphenyl, 4-isopropylphenyl, 4-tert.-butylphenyl, 3-nitrophenyl, 4-nitrophenyl, 3-trifluoromethylphenyl, 4-trifluoromethylphenyl and 4-phenoxyphenyl.

$R^3$ is, for example, methyl, ethyl, n-propyl, isopropyl, chloromethyl, chloropropyl, methoxymethyl, vinyl and propenyl.

Specific examples of the novel compounds include 1-(5-methyl-1,3-dioxan-5-yl)-2-(1,2,4-triazol-1-yl)-3-phenyl-propen-1-one, 1-(5-methyl-1,3-dioxan-5-yl)-2-(1,2,4-triazol-1-yl)-3-phenyl-propen-1-ol, 1-(2-ethyl-5-methyl-1,3-dioxan-5-yl)-2-(1,2,4-triazol-1-yl)-3-phenyl-propen-1-ol, 1-(2-ethyl-5-methyl-1,3-dioxan-5-yl)-2-(1,2,4-triazol-1-yl)-3-phenyl-propen-1-one, 1-(2-n-propyl-5-methyl-1,3-dioxan-5-yl)-2-(1,2,4-triazol-1-yl)-3-phenyl-propen-1-one, 1-(2-n-propyl-5-methyl-1,3-dioxan-5-yl)-2-(1,2,4-triazol-1-yl)-3-phenyl-propen-1-ol, 1-(5-methyl-1,3-dioxan-5-yl)-1-acetoxy-(1,2,4-triazol-1-yl)-3-phenyl-prop-2-ene, 1-(5-methyl-1,3-dioxan-5-yl)-1-propionyloxy-(1,2,4-triazol-1-yl)-3-phenyl-prop-2-ene, 1-(2-ethyl-5-methyl-1,3-dioxan-5-yl)-1-propionyloxy-(1,2,4-triazol-1-yl)-3-phenyl-prop-2-ene, 1-(2-ethyl-5-methyl-1,3-dioxan-5-yl)-1-benzoyloxy-2-(1,2,4-triazol-1-yl)-3-phenyl-prop-2-ene, 1-(2-ethyl-5-methyl-1,3-dioxan-5-yl)-2-chloroacetoxy-2-(1,2,4-triazol-1-yl)-3-phenyl-prop-2-ene, 1-(5-methyl-1,3-dioxan-5-yl)-2-(1,2,4-triazol-1-yl)-3-(furan-2-yl)-propen-1-one, 1-(5-methyl-1,3-dioxan-5-yl)-2-(1,2,4-triazol-1-yl)-3-(furan-2-yl)-propen-1-ol, 1-(5-methyl-1,3-dioxan-5-yl)-1-acetoxy-2-(1,2,4-triazol-1-yl)-3-(furan-2-yl)-prop-2-ene, 1-(5-methyl-1,3-dioxan-5-yl)-2-(1,2,4-triazol-1-yl)-3-(naphth-1-yl)-propen-1-one, 1-(5-methyl-1,3-dioxan-5-yl)-2-(1,2,4-triazol-1-yl)-3-(naphth-1-yl)-propen-1-ol, 1-(2-ethyl-5-methyl-1,3-dioxan-5-yl)-2-(1,2,4-triazol-1-yl)-3-(naphth-1-yl)-propen-1-one, 1-(2-ethyl-5-methyl-1,3-dioxan-5-yl)-2-(1,2,4-triazol-1-yl)-3-(naphth-1-yl)-propen-1-ol, 1-(2,5-diethyl-1,3-dioxan-5-yl)-2-(1,2,4-triazol-1-yl)-3-(naphth-1-yl)-propen-1-one, 1-(2,5-diethyl-1,3-dioxan-5-yl)-2-(1,2,4-triazol-1-yl)-3-(naphth-1-yl)-propen-1-ol, 1-(2-ethyl-5-methyl-1,3-dioxan-5-yl)-1-acetoxy-2-(1,2,4-triazol-1-yl)-3-(naphth-1-yl)-prop-2-ene, 1-(5-methyl-1,3-dioxan-5-yl)-2-(1,2,4-triazol-1-yl)-3-(4-biphenylyl)-propen-1-one, 1-(5-methyl-1,3-dioxan-5-yl)-2-(1,2,4-triazol-1-yl)-3-(4-biphenylyl)-propen-1-ol, 1-(5-methyl-1,3-dioxan-5-yl)-2-(1,2,4-triazol-1-yl)-3-(4-fluorophenyl)-propen-1-one, 1-(5-methyl-1,3-dioxan-5-yl)-2-(1,2,4-triazol-1-yl)-3-(4-fluorophenyl)-propen-1-ol, 1-(5-methyl-1,3-dioxan-5-yl)-1-propionyloxy-2-(1,2,4-triazol-1-yl)-3-(4-fluorophenyl)-prop-2-ene, 1-(5-methyl-1,3-dioxan-5-yl)-2-(1,2,4-triazol-1-yl)-3-(2-chlorophenyl)-propen-1-one, 1-(5-methyl-1,3-dioxan-5-yl)-2-(1,2,4-triazol-1-yl)-3-(2-chlorophenyl)-propen-1-ol, 1-(2-ethyl-5-methyl-1,3-dioxan-5-yl)-2-(1,2,4-triazol-1-yl)-3-(2-chlorophenyl)-propen-1-one, 1-(2-ethyl-5-methyl-1,3-dioxan-5-yl)-2-(1,2,4-triazol-1-yl)-3-(2-chlorophenyl)-propen-1-ol, 1-(2-ethyl-5-methyl-1,3-dioxan-5-yl)-1-acetoxy-2-(1,2,4-triazol-1-yl)-3-(2-chlorophenyl)-prop-2-ene, 1-(5-methyl-1,3-dioxan-5-yl)-2-(1,2,4-triazol-1-yl)-3-(3-chlorophenyl)-propen-1-one, 1-(5-methyl-1,3-dioxan-5-yl)-2-(1,2,4-triazol-1-yl)-3-(3-chlorophenyl)-propen-1-ol, 1-(5-methyl-1,3-dioxan-5-yl)-1-propionyloxy-2-(1,2,4-triazol-1-yl)-3-(3-chlorophenyl)-prop-2-ene, 1-(5-methyl-1,3-dioxan-5-yl)-2-(1,2,4-triazol-1-yl)-3-(4-chlorophenyl)-propen-1-one, 1-(5-methyl-1,3-dioxan-5-yl)-2-(1,2,4-triazol-1-yl)-3-(4-chlorophenyl)-propen-1-ol, 1-(2,5-dimethyl-1,3-dioxan-5-yl)-2-(1,2,4-triazol-1-yl)-3-

(4-chlorophenyl)-propen-1-one, 1-(2,5-dimethyl-1,3-dioxan-5-yl)-2-(1,2,4-triazol-1-yl)-3-(4-chlorophenyl)-propen-1-ol, 1-(2-ethyl-5-methyl-1,3-dioxan-5-yl)-2-(1,2,4-triazol-1-yl)-3-(4-chlorophenyl)-propen-1-one, 1-(2-ethyl-5-methyl-1,3-dioxan-5-yl)-2-(1,2,4-triazol-1-yl)-3-(4-chlorophenyl)-propen-1-ol, 1-(2-n-propyl-5-methyl-1,3-dioxan-5-yl)-2-(1,2,4-triazol-1-yl)-3-(4-chlorophenyl)-propen-1-one, 1-(2-n-propyl-5-methyl-1,3-dioxan-5-yl)-2-(1,2,4-triazol-1-yl)-3-(4-chlorophenyl)-propen-1-ol, 1-(2,5-diethyl-1,3-dioxan-5-yl)-2-(1,2,4-triazol-1-yl)-3-(4-chlorophenyl)-propen-1-ol, 1-(2,5-diethyl-1,3-dioxan-5-yl)-2-(1,2,4-triazol-1-yl)-3-(4-chlorophenyl)-propen-1-one, 1-(2-ethyl-5-methyl-1,3-dioxan-5-yl)-1-acetoxy-2-(1,2,4-triazol-1-yl)-3-(4-chlorophenyl)-prop-2-ene, 1-(2-ethyl-5-methyl-1,3-dioxan-5-yl)-1-propionyloxy-2-(1,2,4-triazol-1-yl)-3-(4-chlorophenyl)-prop-2-ene, 1-(2-ethyl-5-methyl-1,3-dioxan-5-yl)-1-dichloroacetoxy-2-(1,2,4-triazol-1-yl)-3-(4-chlorophenyl)-prop-2-ene, 1-(5-methyl-1,3-dioxan-5-yl)-2-(1,2,4-triazol-1-yl)-3-(4-bromophenyl)-propen-1-one, 1-(5-methyl-1,3-dioxan-5-yl)-2-(1,2,4-triazol-1-yl)-3-(4-bromophenyl)-propen-1-ol, 1-(2-ethyl-5-methyl-1,3-dioxan-5-yl)-2-(1,2,4-triazol-1-yl)-3-(4-bromophenyl)-propen-1-one, 1-(2-ethyl-5-methyl-1,3-dioxan-5-yl)-2-(1,2,4-triazol-1-yl)-3-(4-bromophenyl)-propen-1-ol, 1-(2-n-propyl-5-methyl-1,3-dioxan-5-yl)-2-(1,2,4-triazol-1-yl)-3-(4-bromophenyl)-propen-1-one, 1-(2-n-propyl-5-methyl-1,3-dioxan-5-yl)-2-(1,2,4-triazol-1-yl)-3-(4-bromophenyl)-propen-1-ol, 1-(2,5-diethyl-1,3-dioxan-5-yl)-2-(1,2,4-triazol-1-yl)-3-(4-bromophenyl)-propen-1-ol, 1-(2,5-diethyl-1,3-dioxan-5-yl)-2-(1,2,4-triazol-1-yl)-3-(4-bromophenyl)-propen-1-one, 1-(2-ethyl-5-methyl-1,3-dioxan-5-yl)-1-acetoxy-2-(1,2,4-triazol-1-yl)-3-(4-bromophenyl)-prop-2-ene, 1-(2-ethyl-5-methyl-1,3-dioxan-5-yl)-1-propionyloxy-2-(1,2,4-triazol-1-yl)-3-(4-bromophenyl)-prop-2-ene, 1-(5-methyl-1,3-dioxan-5-yl)-2-(1,2,4-triazol-1-yl)-3-(3,4-dichlorophenyl)-propen-1-one, 1-(5-methyl-1,3-dioxan-5-yl)-2-(1,2,4-triazol-1-yl)-3-(3,4-dichlorophenyl)-propen-1-ol, 1-(2-ethyl-5-methyl-1,3-dioxan-5-yl)-2-(1,2,4-triazol-1-yl)-3-(3,4-dichlorophenyl)-propen-1-one, 1-(2-ethyl-5-methyl-1,3-dioxan-5-yl)-2-(1,2,4-triazol-1-yl)-3-(3,4-dichlorophenyl)-propen-1-ol, 1-(5-methyl-1,3-dioxan-5-yl)-1-acetoxy-2-(1,2,4-triazol-1-yl)-3-(3,4-dichlorophenyl)-prop-2-ene, 1-(2-ethyl-5-methyl-1,3-dioxan-5-yl)-1-acetoxy-2-(1,2,4-triazol-1-yl)-3-(3,4-dichlorophenyl)-prop-2-ene, 1-(5-methyl-1,3-dioxan-5-yl)-2-(1,2,4-triazol-1-yl)-3-(2,4-dichlorophenyl)-propen-1-one, 1-(5-methyl-1,3-dioxan-5-yl)-2-(1,2,4-triazol-1-yl)-3-(2,4-dichlorophenyl)-propen-1-ol, 1-(2-ethyl-5-methyl-1,3-dioxan-5-yl)-2-(1,2,4-triazol-1-yl)-3-(2,4-dichlorophenyl)-propen-1-one, 1-(2-ethyl-5-methyl-1,3-dioxan-5-yl)-2-(1,2,4-triazol-1-yl)-3-(2,4-dichlorophenyl)-propen-1-ol, 1-(2,5-diethyl-1,3-dioxan-5-yl)-2-(1,2,4-triazol-1-yl)-3-(2,4-dichlorophenyl)-propen-1-one, 1-(2,5-diethyl-1,3-dioxan-5-yl)-2-(1,2,4-triazol-1-yl)-3-(2,4-dichlorophenyl)-propen-1-ol, 1-(2-isopropyl-5-methyl-1,3-dioxan-5-yl)-2-(1,2,4-triazol-1-yl)-3-(2,4-dichlorophenyl)-propen-1-one, 1-(2-isopropyl-5-methyl-1,3-dioxan-5-yl)-2-(1,2,4-triazol-1-yl)-3-(2,4-dichlorophenyl)-propen-1-ol, 1-(2-n-butyl-5-methyl-1,3-dioxan-5-yl)-2-(1,2,4-triazol-1-yl)-3-(2,4-dichlorophenyl)-propen-1-one, 1-(2-n-butyl-5-methyl-1,3-dioxan-5-yl)-2-(1,2,4-triazol-1-yl)-3-(2,4-dichlorophenyl)-propen-1-ol, 1-(5-methyl-1,3-dioxan-5-yl)-1-acetoxy-2-(1,2,4-triazol-1-yl)-3-(2,4-dichlorophenyl)-prop-2-ene, 1-(5-methyl-1,3-dioxan-5-yl)-1-butyryloxy-2-(1,2,4-triazol-1-yl)-3-(2,4-dichlorophenyl)-prop-2-ene, 1-(2-ethyl-5-methyl-1,3-dioxan-5-yl)-1-acetoxy-2-(1,2,4-triazol-1-yl)-3-(2,4-dichlorophenyl)-prop-2-ene, 1-(2-ethyl-5-methyl-1,3-dioxan-5-yl)-1-propionyloxy-2-(1,2,4-triazol-1-yl)-3-(2,4-dichlorophenyl)-prop-2-ene, 1-(5-methyl-1,3-dioxan-5-yl)-2-(1,2,4-triazol-1-yl)-3-(2,3,4-trichlorophenyl)-propen-1-one, 1-(5-methyl-1,3-dioxan-5-yl)-2-(1,2,4-triazol-1-yl)-3-(2,3,4-trichlorophenyl)-propen-1-ol, 1-(5-methyl-1,3-dioxan-5-yl)-1-acetoxy-2-(1,2,4-triazol-1-yl)-3-(2,3,4-trichlorophenyl)-prop-2-ene, 1-(2-ethyl-5-methyl-1,3-dioxan-5-yl)-2-(1,2,4-triazol-1-yl)-3-(2,3,4-trichlorophenyl)-propen-1-one, 1-(2-ethyl-5-methyl-1,3-dioxan-5-yl)-2-(1,2,4-triazol-1-yl)-3-(2,3,4-trichlorophenyl)-propen-1-ol, 1-(5-methyl-1,3-dioxan-5-yl)-2-(1,2,4-triazol-1-yl)-3-(3-trifluoromethylphenyl)-propen-1-one, 1-(5-methyl-1,3-dioxan-5-yl)-2-(1,2,4-triazol-1-yl)-3-(3-trifluoromethylphenyl)-propen-1-ol, 1-(5-methyl-1,3-dioxan-5-yl)-1-propionyloxy-2-(1,2,4-triazol-1-yl)-3-(3-trifluoromethylphenyl)-prop-2-ene, 1-(5-methyl-1,3-dioxan-5-yl)-2-(1,2,4-triazol-1-yl)-3-(4-trifluoromethylphenyl)-propen-1-one, 1-(5-methyl-1,3-dioxan-5-yl)-2-(1,2,4-triazol-1-yl)-3-(4-trifluoromethylphenyl)-propen-1-ol, 1-(2-ethyl-5-methyl-1,3-dioxan-5-yl)-2-(1,2,4-triazol-1-yl)-3-(4-trifluoromethylphenyl)-propen-1-one, 1-(2-ethyl-5-methyl-1,3-dioxan-5-yl)-2-(1,2,4-triazol-1-yl)-3-(4-trifluoromethylphenyl)-propen-1-ol, 1-(5-methyl-1,3-dioxan-5-yl)-2-(1,2,4-triazol-1-yl)-3-(4-methylphenyl)-propen-1-one, 1-(5-methyl-1,3-dioxan-5-yl)-2-(1,2,4-triazol-1-yl)-3-(4-methylphenyl)-propen-1-ol, 1-(2-ethyl-5-methyl-1,3-dioxan-5-yl)-2-(1,2,4-triazol-1-yl)-3-(4-methylphenyl)-propen-1-one, 1-(2-ethyl-5-methyl-1,3-dioxan-5-yl)-2-(1,2,4-triazol-1-yl)-3-(4-methylphenyl)-propen-1-ol, 1-(5-methyl-1,3-dioxan-5-yl)-2-(1,2,4-triazol-1-yl)-3-(4-ethylphenyl)-propen-1-one, 1-(5-methyl-1,3-dioxan-5-yl)-2-(1,2,4-triazol-1-yl)-3-(4-ethylphenyl)-propen-1-ol, 1-(5-methyl-1,3-dioxan-5-yl)-2-(1,2,4-triazol-1-yl)-3-(4-tert.-butylphenyl)-propen-1-one, 1-(5-methyl-1,3-dioxan-5-yl)-2-(1,2,4-triazol-1-yl)-3-(4-tert.-butylphenyl)-propen-1-ol, 1-(5-methyl-1,3-dioxan-5-yl)-2-(1,2,4-triazol-1-yl)-3-(4-methoxyphenyl)-propen-1-ol, 1-(5-methyl-1,3-dioxan-5-yl)-2-(1,2,4-triazol-1-yl)-3-(4-methoxyphenyl)-propen-1-one, 1-(2-ethyl-5-methyl-1,3-dioxan-5-yl)-2-(1,2,4-triazol-1-yl)-3-(4-methoxyphenyl)-propen-1-one, 1-(2-ethyl-5-methyl-1,3-dioxan-5-yl)-2-(1,2,4-triazol-1-yl)-3-(4-methoxyphenyl)-propen-1-ol, 1-(5-methyl-1,3-dioxan-5-yl)-2-(1,2,4-triazol-1-yl)-3-(4-ethoxyphenyl)-propen-1-one, 1-(5-methyl-1,3-dioxan-5-yl)-2-(1,2,4-triazol-1-yl)-3-(4-ethoxyphenyl)-propen-1-ol, 1-(5-methyl-1,3-dioxan-5-yl)-2-(1,2,4-triazol-1-yl)-3-(4-n-butoxyphenyl)-propen-1-one, 1-(5-methyl-1,3-dioxan-5-yl)-2-(1,2,4-triazol-1-yl)-3-(4-n-butoxyphenyl)-propen-1-ol, 1-(5-methyl-1,3-dioxan-5-yl)-2-(1,2,4-triazol-1-yl)-3-(4-tert.-butoxyphenyl)-propen-1-ol, 1-(5-methyl-1,3-dioxan-5-yl)-2-(1,2,4-triazol-1-yl)-3-(4-tert.-butoxyphenyl)-propen-1-one, 1-(5-methyl-1,3-dioxan-5-yl)-2-(1,2,4-triazol-1-yl)-3-(4-nitrophenyl)-propen-1-one and 1-(5-methyl-1,3-dioxan-5-yl)-2-(1,2,4-triazol-1-yl)-3-(4-nitrophenyl)-propen-1-ol.

The compounds of the formula I can be prepared by condensing an aldehyde of the formula II $$Ar-CH=O \qquad \text{II}$$

where Ar has the above meaning, with a 1-(1,3-dioxan-5-yl)-2-(1,2,4-triazol-1-yl)-ethan-1-one derivative of the formula III

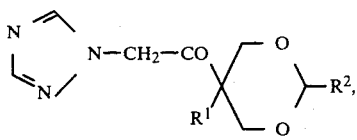

where $R^1$ and $R^2$ have the above meanings, and, if desired, subsequently reducing the resulting compounds to the alcohol and then, if desired, esterifying the alcohol with an acid halide of the formula IV $$Y-CO-R^3 \qquad\qquad IV$$

where $R^3$ has the above meaning and Y is chlorine or bromine, or with an acid anhydride of the formula V $$(R^3-CO)_2O \qquad\qquad V$$

where $R^3$ has the above meaning, and, if desired, converting the ketone, alcohol or ester compounds obtained to their salts or metal complexes.

The condensation of the compound II with the compound III is carried out in the presence or absence of a solvent or diluent and with or without addition of an inorganic or organic base and/or acid, at from $-10°$ to 150° C., with or without azeotropic removal of the water of reaction. The preferred solvents and diluents include water, alcohols, eg. methanol, ethanol, isopropanol and tert.-butanol, hydrocarbons, eg. n-hexane, n-heptane, n- and iso-octane, cyclohexane, tetrahydronaphthalene, decahydronaphthalene, toluene, xylene and cumene, amides, eg. dimethylformamide, dimethylacetamide and N-methylpyrrolidone, and ethers, eg. diethyl ether, methyl tert.-butyl ether, dioxane and tetrahydrofuran, and mixtures of these.

Examples of suitable bases and acids, which may or may not be present in from catalytic to stoichiometric amounts are alkali metal hydroxides and alkaline earth metal hydroxides, such as sodium hydroxide, potassium hydroxide, calcium hydroxide and barium hydroxide, alkoxides, such as sodium methoxide, ethoxide, isopropoxide and tert.-butoxide and the corresponding potassium compounds, acetates, such as sodium acetate and potassium acetate, amines, such as pyrrolidine, piperidine, triethylamine and N,N-dimethylcyclohexylamine, inorganic acids, such as hydrochloric acid, phosphoric acid and sulfuric acid, and organic acids, such as formic acid, acetic acid, p-toluenesulfonic acid and trifluoromethylsulfonic acid.

The reactions are in general carried out at from 20° to 150° C., under atmospheric or superatmospheric pressure, continuously or batchwise.

The 1-(1,3-dioxan-5-yl)-2-(1,2,4-triazol-1-yl)-ethan-1-ones of the formula III are novel compounds. They can be obtained, for example, by reacting a 1-(1,3-dioxan-5-yl)-2-halogen-ethan-1-one of the formula VI

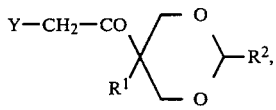

where $R^1$ and $R^2$ have the above meanings and Y is chlorine or bromine, with the sodium salt of 1,2,4-triazole.

The compounds of the formula VI are also novel. They are obtained, for example, by reacting a known (1,3-dioxan-5-yl)-ethan-1-one of the formula VII

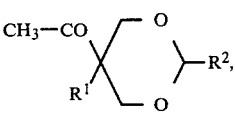

where $R^1$ and $R^2$ have the above meanings, with sulfuryl chloride, by the method of D. P. Wyman and P. R. Kaufman, J. Org. Chem. 29 (1964), 1956, or with bromine in formamide by the method of H. Bredereck et al., Chem. Ber. 93 (1960), 2083.

The reduction of a ketone of the formula Ia

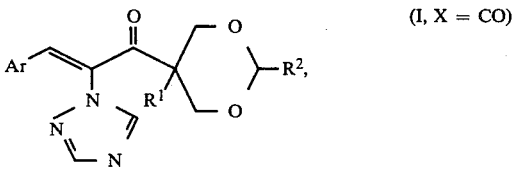

where Ar, $R^1$ and $R^2$ have the above meanings, can be carried out in the presence or absence of a solvent or diluent, at from $-20°$ to 150° C., giving an alcohol of the formula Ib

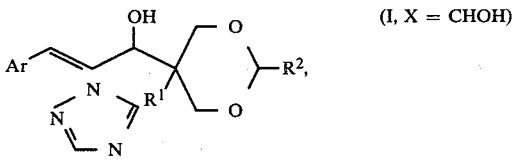

where Ar, $R^1$ and $R^2$ have the above meanings. The reduction itself can be effected with hydrogen in the presence of a catalyst, with complex borohydrides or aluminum hydrides, with aluminum isopropoxide and isopropanol, with sodium dithionite or by electrochemical means.

Examples of suitable solvents or diluents for these reductions are water, methanol, ethanol, propanol, isopropanol, acetic acid, diethyl ether, tetrahydrofuran, dioxane, ethyl acetate, toluene, dimethylformamide or mixtures of these.

The catalytic hydrogenation is carried out under a pressure of from 2 to 80 bar, with a platinum or palladium catalyst on an inert carrier, and is continued until hydrogen absorption has ceased. Examples of the hydrides which may be used as reducing agents are sodium borohydride and lithium aluminum hydride.

The esterification of an alcohol of the formula I (X=CHOH) is carried out in the presence or absence of a solvent or diluent, and with or without addition of an acid acceptor and/or reaction accelerator. Suitable solvents for the reduction reaction are diethyl ether, tetrahydrofuran, dioxane, n-pentane, n-hexane, petroleum ether, cyclohexane, toluene, methylene chloride, chloroform, acetone, methyl ethyl ketone, acetonitrile, dimethylformamide, acetic anhydride and propionic anhydride.

Suitable acid acceptors are bases, for example alkali metal carbonates and alkaline earth metal carbonates, eg. sodium carbonate, potassium carbonate, sodium bicarbonate, potassium bicarbonate, calcium carbonate and barium carbonate, and tertiary amines, eg. triethylamine, N,N-dimethylcyclohexylamine, N,N-dimethylaniline, N-methylpiperidine and pyridine.

Suitable reaction accelerators include azoles, eg. 1,2,4-triazole and imidazole, and tertiary amines, eg. 4-dimethylaminopyridine and 4-pyrrolidinopyridine.

The resulting compounds of the formula I are isolated by conventional methods, purified if necessary, and converted, if desired, to salts or metal complexes by reaction with acids or metal salts respectively.

The Examples which follow illustrate the invention.

EXAMPLE 1

(a) Preparation of the starting material

A solution of 498 g (1 mole) of pyrrolidonebromine complex in 1 liter of tetrahydrofuran is added dropwise in the course of 2 hours to a solution of 144 g (1 mole) of 5-acetyl-5-methyl-1,3-dioxane and 85.5 g (1 mole) of pyrrolidone in 500 ml of tetrahydrofuran, at 50° C. After the mixture has been stirred for a further 8 hours at 50° C., the white precipitate of pyrrolidone hydrobromide is filtered off and washed with 50 ml of tetrahydrofuran, and the filtrate is concentrated in vacuo. 220 g (99%) of crude oily 1-(5-methyl-1,3-dioxan-5-yl)-2-bromo-ethan-1-one are obtained.

A solution of 223 g (1 mole) of 1-(5-methyl-1,3-dioxan-5-yl)-2-bromoethan-1-one in 200 ml of tetrahydrofuran is added dropwise in the course of 2 hours to a suspension, stirred under pure nitrogen, of 100 g (1.1 moles) of sodium 1,2,4-triazolide in 300 ml of dry tetrahydrofuran, at 25° C. The mixture is refluxed for 8 hours, the inorganic precipitate is then filtered off, and the filtrate is concentrated to half its volume. It is then seeded and left to stand overnight at +3° C. The precipitate is filtered off, washed with 30 ml of cold (+5° C.) tetrahydrofuran, then with 80 ml of ether and thereafter with 100 ml of n-pentane, and dried. 184 g (87.2%) of 1-(5-methyl-1,3-dioxan-5-yl)-2-(1,2,4-triazol-1-yl)-ethan-1-one are obtained as white crystals of melting point 95°–97° C.

(b) Preparation of the end product

A mixture of 12.7 g (0.06 mole) of 1-(5-methyl-1,3-dioxan-5-yl)-2-(1,2,4-triazol-1-yl)-ethan-1-one, 10.8 g (0.06 mole) of 2,4-dichlorobenzaldehyde, 1 g of piperidine, 0.5 g of acetic acid and 150 ml of toluene is stirred for 10 hours under reflux, with elimination of water. The mixture is then cooled, washed with three times 80 ml of water, dried over sodium sulfate and concentrated under reduced pressure. The residue is dissolved in 250 ml of acetonitrile and the solution is decolorized with 1 g of animal charcoal at 40° C., concentrated to 40 ml and cooled to 0° C. The colorless precipitate is filtered off, washed with 40 ml of ether and dried. 18.4 g (83.3%) of 1-(5-methyl-1,3-dioxan-5-yl)-2-(1,2,4-triazol-1-yl)-3-(2,4-dichlorophenyl)-propen-1-one, of melting point 133°–135° C., are obtained.

EXAMPLE 2

4.5 g (0.118 mole) of sodium borohydride are added, in portions, to a solution of 36.1 g (0.1 mole) of 1-(5-methyl-1,3-dioxan-5-yl)-2-(1,2,5-triazol-1-yl)-3-(2,4-dichlorophenyl)-propen-1-one in 250 ml of methanol at from −5° to 0° C. The mixture is stirred for 14 hours at 22° C. and the white precipitate is filtered off and the filtrate is concentrated under reduced pressure. The precipitate and the residue are combined and stirred for half an hour with 3 liters of methylene chloride and 500 ml of 10% strength potassium hydroxide solution at 25° C. The organic layer is separated off, washed with three times 100 ml of water, dried over sodium sulfate and concentrated. The residue crystallizes out after addition of 10 ml of ether. 31.3 g (84.6%) of 1-(5-methyl-1,3-dioxan-5-yl)-2-(1,2,4-triazol-1-yl)-3-(2,4-dichlorophenyl)-propen-1-ol are obtained as colorless crystals of melting point 190°–192° C.

EXAMPLE 3

A mixture of 14 g (0.0378 mole) of 1-(5-methyl-1,3-dioxan-5-yl)-2-(1,2,4-triazol-1-yl)-3-(3,4-dichlorophenyl)-propen-1-ol (Example 25), 1 g of imidazole and 80 g of acetic anhydride is stirred for 8 hours at 70° C. and then concentrated under reduced pressure. The residue is taken up in 300 ml of ether and stirred for half an hour with 100 ml of 6% strength sodium bicarbonate solution. The organic phase is dried over sodium sulfate and concentrated under reduced pressure, finally at 50° C. under 0.1 mbar. 10.8 g (69.3% of theory) of 1-(5-methyl-1,3-dioxan-5-yl)-1-acetoxy-2-(1,2,4-triazol-1-yl)-3-(3,4-dichlorophenyl)-prop-2-ene are obtained as a pale yellow resin.

$^1$H-NMR (80 MHz/CDCl$_3$):=0.6 (s, 3H), 2.08 (s, 3H), 3.2–3.4 (m, 2H), 3.8–4.0 (g, 2H), 4.4–4.9 (2dd, conjointly 2H), 5.5 (s, 1H), 6.3–7.4 (m, conjointly 4H), 8.0 (s, 1H) and 8.2 ppm (s, 1H).

The compounds listed in the Table which follows can be prepared in a similar manner.

TABLE

| Ex. no. | Ar | R$^1$ | R$^2$ | X | m.p./°C. | IR (film) [cm$^{-1}$] |
|---|---|---|---|---|---|---|
| 4 | C$_6$H$_5$— | CH$_3$— | H | —CO— | resin | 3100,2965,1660,1585,1485, 1195,1150,1065,920,750, 690,668. |
| 5 | α-Furyl | CH$_3$— | H | —CO— | 108–110 | |
| 6 | α-Furyl | CH$_3$— | H | OH<br>\|<br>—CH— | 99–102 | |
| 7 | α-Furyl | CH$_3$— | H | —CO— | 118–125 | |
| 8 | α-Naphthyl | CH$_3$— | C$_2$H$_5$— | —CO— | resin | 3112,2970,2850,1668,1490, 1380,1265,1155,1080,918, 792,770,665. |
| 9 | α-Naphthyl | CH$_3$— | C$_2$H$_5$ | OH<br>\|<br>—CH— | resin | 3300,3060,2965,2850,1508, 1468,1275,1160,1090,925, 880,778,675. |
| 10 | p-C$_6$H$_5$—C$_6$H$_4$ | CH$_3$— | H | —CO— | resin | 3100,3010,2845,1668,1590, |

TABLE-continued

| Ex. no. | Ar | R¹ | R² | X | m.p./°C. | IR (film) [cm⁻¹] |
|---|---|---|---|---|---|---|
| | | | | | | 1488,1150,1015,920,910, 830,755,725,690,665. |
| 11 | p-C₆H₅—C₆H₄ | CH₃— | H | —CH(OH)— | 122–124 | |
| 12 | 2-Cl—C₆H₄ | CH₃— | H | —CO— | 86–88 | |
| 13 | 3-Cl—C₆H₄ | CH₃ | H | —CO— | resin | 3118,3060,2980,2850,1680, 1600,1592,1270,1155,1070, 920,780,680,665 |
| 14 | 3-Cl—C₆H₄ | CH₃— | H | —CH(OH)— | resin | 3250,3120,2845,1493,1266, 1155,1078,1023,918,780, 668. |
| 15 | 4-Cl—C₆H₄ | CH₃— | H | —CO— | resin | 3100,2960,2840,1665,1572, 1475,1390,1265,1155,1082, 1025,1000,920,820,752,668 |
| 16 | 4-Cl—C₆H₄ | CH₃— | C₂H₅— | —CO— | resin | 3108,2960,2845,1685,1578, 1490,1262,1150,1080,940, 915,815,752,665,640. |
| 17 | 4-Cl—C₆H₄ | CH₃ | C₂H₅— | —CH(OH)— | resin | 3380,3120,2960,2840,1490, 1480,1254,1150,1125,1080, 915,870,810,665. |
| 18 | 4-Br—C₆H₄ | CH₃— | H | —CO— | resin | 3100,2970,2840,1665,1567, 1485,1470,1265,1155,1060, 1025,1000,918,815,750,670 |
| 19 | 4-Br—C₆H₄ | CH₃— | H | —CH(OH)— | resin | 3400,2970,2850,1495,1480, 1270,1158,1132,1068,1022, 1004,918,810,668. |
| 20 | 4-Br—C₆H₄ | CH₃— | H | —CH(O—COCH₃)— | resin | 3110,2960,2840,1730,1490, 1475,1360,1218,1150,1020, 915,806,662. |
| 21 | 4-Br—C₆H₄ | CH₃— | H | —CH(O—COCH₂CH₃)— | resin | 3118,2970,2845,1730,1578, 1490,1478,1265,1150,1070, 1000,918,810,665. |
| 22 | 4-Br—C₆H₄ | CH₃— | C₂H₅— | —CO— | resin | 3115,2970,2850,1690,1580, 1492,1268,1128,1085,1065, 1002,920,816,752,670. |
| 23 | 4-Br—C₆H₄ | CH₃— | C₂H₅— | —CH(OH)— | resin | 3300,2960,2845,1492,1476, 1390,1265,1150,1082,1060, 1000,915,870,810,665. |
| 24 | 3,4-DiCl—C₆H₃— | CH₃— | H | —CO— | resin | 3110,2975,2855,1680,1600, 1475,1462,1270,1200,1155, 1070,920,880,760,665. |
| 25 | 3,4-DiCl—C₆H₃— | CH₃— | H | —CH(OH)— | resin | 3400,2958,2840,1490,1460, 1152,1125,1075,1020,914, 884,810,665. |
| 26 | 3,4-DiCl—C₆H₃— | CH₃— | C₂H₅— | —CO— | resin | 3105,2970,2850,1690,1430, 1450,1380,1265,1150,1080, 1022,920,870,810,665. |
| 27 | 3,4-DiCl—C₆H₃ | CH₃— | C₂H₅— | —CH(OH)— | resin | 3300,2970,2855,1505,1470, 1400,1275,1135,1090,1030, 925,880. |
| 28 | 4-Cl—C₆H₄ | C₂H₅— | C₂H₅— | —CO— | resin | 3108,2960,2924,2845,1675, 1480,1392,1265,1123,1080, 916,815,775,664. |
| 29 | 2,4-DiCl—C₆H₃ | C₂H₅— | C₂H₅— | —CO— | resin | 3100,2964,2930,2850,1680, 1576,1640,1375,1266,1125 1095,918,876,860,826,812, 664, |
| 30 | 2,4-DiCl—C₆H₃ | CH₃— | C₂H₅— | —CO— | resin | 3100,2970,2850,1680,1575, 1490,1460,1265,1155,1125, 1090,992,918,860,665. |

TABLE-continued

| Ex. no. | Ar | $R^1$ | $R^2$ | X | m.p./°C. | IR (film) [cm$^{-1}$] |
|---|---|---|---|---|---|---|
| 31 | 2,4-DiCl—C$_6$H$_3$ | CH$_3$— | C$_2$H$_5$— | —CH(OH)— | resin | 3300,2970,2845,1580,1495, 1460,1265,1152,1085,1045, 918, |
| 32 | 2,4-DiCl—C$_6$H$_3$ | CH$_3$— | —CH(CH$_3$)$_2$ | —CO— | resin | 3100,2970,2860,1690,1580, 1465,1380,1270,1185,1130, 1095,995,920,860,830,670 |
| 33 | 2,4-DiCl—C$_6$H$_3$ | CH$_3$— | —CH(CH$_3$)$_2$ | —CH(OH)— | resin | 3300,2960,2845,1580,1500, 1465,1268,1130,1095,995, 918,860,815,670. |
| 34 | 2,4-DiCl—C$_6$H$_3$ | CH$_3$— | n-C$_4$H$_9$ | —CO— | resin | 3120,2950,2860,1710,1685, 1578,1496,1462,1380,1268, 1130,1097,945,860,770,680 |
| 35 | 2,4-DiCl—C$_6$H$_3$ | CH$_3$— | n-C$_4$H$_9$ | —CH(OH)— | resin | 3200,2945,2850,1498,1467, 1365,1268,1125,1098,1018, 990,925,855,815. |
| 36 | 2,3,4-TriCl—C$_6$H$_2$ | CH$_3$— | H | —CO— | 110–140 | |
| 37 | 2,3,4-TriCl—C$_6$H$_2$ | CH$_3$— | H | —CH(OH)— | 156–159 | |
| 38 | 2,3,4-TriCl—C$_6$H$_2$ | CH$_3$— | H | —CH(O—COCH$_3$)— | 138–140 | |
| 39 | 3-CF$_3$C$_6$H$_4$ | CH$_3$— | H | —CO— | resin | 3115,2980,2850,1680,1493, 1324,1156,1118,1068,1025, 918,795,695,670,655. |
| 40 | 3-CF$_3$C$_6$H$_4$ | CH$_3$— | H | —CH(OH)— | 95–98 | |
| 41 | 3-CF$_3$C$_6$H$_4$ | CH$_3$— | H | —CH(O—CO—CH$_2$CH$_3$)— | resin | 3110,2970,2840,1730,1490, 1320,1190,1150,1115,1065, 915,795,690,665,650. |
| 42 | 4-CF$_3$—C$_6$H$_4$ | CH$_3$— | H | —CO— | resin | 3110,2980,2845,1680,1605, 1490,1315,1155,1115,1056, 915,828,665. |
| 43 | 4-CF$_3$—C$_6$H$_4$ | CH$_3$— | H | —CH(OH)— | 108–118 | |
| 44 | 4-CH$_3$—C$_6$H$_4$ | CH$_3$— | H | —CO— | 82–84 | |
| 45 | 4-CH$_3$—C$_6$H$_4$ | CH$_3$— | H | —CH(OH)— | resin | 3260,3120,2845,1505,1492, 1290,1150,1130,1068,1024, 930,918,880,808,668. |
| 46 | 4-CH$_3$—C$_6$H$_4$ | CH$_3$— | C$_2$H$_5$— | —CO— | resin | 3110,2695,2845,1675,1595, 1490,1380,1262,1142,1125, 1080,918,805,666. |
| 47 | 4-CH$_3$—C$_6$H$_4$ | CH$_3$— | C$_2$H$_5$— | —CH(OH)— | resin | 3300,2960,2840,1500,1455, 1390,1265,1154,1128,1084, 1022,918,872,805,668. |
| 48 | 4-tert.Butyl—C$_6$H$_4$ | CH$_3$— | H | —CO— | resin | 3118,2960,2860,1670,1590, 1490,1355,1260,1165,1065, 1025,995,915,825,750,668. |
| 49 | 4-tert.Butyl—C$_6$H$_4$ | CH$_3$— | H | —CH(OH)— | resin | 3300,2955,2850,1492,1450, 1352,1260,1155,1072,1025, 918,820,668. |
| 50 | 4-CH$_3$O—C$_6$H$_4$ | CH$_3$— | H | —CO— | 132–134 | |
| 51 | 4-CH$_3$O—C$_6$H$_4$ | CH$_3$— | C$_2$H$_5$— | —CO— | resin | 3115,2970,2840,1670,1590, 1505,1250,1170,1165,1125, 1080,1020,918,826,668. |
| 52 | 4-CH$_3$O—C$_6$H$_4$ | CH$_3$— | C$_2$H$_5$— | —CH(OH)— | resin | 3320,2840,1595,1500,1455, 1385,1240,1080,1020,915, 870,820,668. |

TABLE-continued

| Ex. no. | Ar | R¹ | R² | X | m.p./°C. | IR (film) [cm⁻¹] |
|---|---|---|---|---|---|---|
| 53 | 4-$C_2H_5$—O—$C_6H_4$ | $CH_3$— | H | —CO— | 117–120 | |
| 54 | 4-$C_2H_5$—O—$C_6H_4$ | $CH_3$— | H | —CH(OH)— | 123–125 | |
| 55 | 4-$O_2N$—$C_6H_4$ | $CH_3$— | H | —CO— | resin | 3110,2975,2850,1680,1590, 1510,1340,1155,1025,915, 840,742,668. |
| 56 | 4-$O_2N$—$C_6H_4$ | $CH_3$— | H | —CH(OH)— isomer I | 201–203 | |
| 57 | 4-$O_2N$—$C_6H_4$ | $CH_3$— | H | —CH(OH)— isomer mixture | resin | 3250,2850,1590,1510,1335, 1152,1130,1070,1020,918, 842,749,690,665. |
| 58 | 4-$F_3C$—$C_6H_4$— | $CH_3$— | $C_2H_5$— | —CO— | resin | 3110,2965,1680,1488, 1312,1155,1115,915,825, 660 |
| 59 | 4-$F_3C$—$C_6H_4$ | $CH_3$— | $C_2H_5$— | —CH(OH)— isomer I | 180–182 | |
| 60 | 4-$F_3C$—$C_6H_4$ | $CH_3$— | $C_2H_5$— | —CH(OH)— isomer mixture | resin | 3230,2980,1622,1507, 1320,1170,1130,1066, 1020,925,883,825,672 |
| 61 | $C_2H_5$—O—$C_6H_4$ | $CH_3$— | $C_2H_5$— | —CO— | resin | 3115,2980,1670,1590, 1500,1383,1250,1174, 1130,1084,1035,920, 830,672 |
| 62 | $C_2H_5$—O—$C_6H_4$ | $CH_3$— | $C_2H_5$— | —CH(OH)— | resin | 3300,2970,1600,1500, 1240,1182,1085,1038, 918,875,816,668 |
| 63 | 4-$O_2N$—$C_6H_4$ | $CH_3$— | $C_2H_5$— | CO | resin | 3115,2975,1690,1595, 1515,1342,1225,1160, 1130,1000,922,856, 820,745 |
| 64 | 4-$O_2N$—$C_6H_4$ | $CH_3$— | $C_2H_5$— | —CH(OH)— | resin | 3300,2960,1590,1510, 1336,1270,1130,1083, 918,873,845,735 |
| 65 | $C_6H_5$ | $CH_3$— | $C_2H_5$— | —CO— | resin | 3120,2975,1698,1495, 1445,1382,1268,1158, 1130,1086,922,755, 695,672 |
| 66 | $C_6H_5$ | $CH_3$— | $C_2H_5$ | —CH(OH)— | resin | 3280,2960,1492,1450, 1268,1155,1130,1085, 920,874,740,692,668 |

The novel compounds according to the invention influence plant metabolism, and may therefore be used as plant growth regulators. They may have an influence on practically all the development stages of a plant.

The diversity of action of growth regulators depends especially on
(a) the type and variety of plant;
(b) the time applied, with reference to the development stage of the plants and the time of year;
(c) the place and method of application (seed treatment, soil treatment, or application to leaves);
(d) climatic factors (sunshine duration, average temperature, precipitate);
(e) soil conditions (including fertilization);
(f) the formulation or application form of the active ingredient; and
(g) the concentration at which the active ingredient is applied.

A description of some of the various possibilities of using growth regulators in agriculture and horticulture is given below.

A. With the compounds according to the invention, vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embarkments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton.

It is thus possible for this important crop to be harvested completely mechanically.

Growth regulators may also increase or inhibit lateral branching. This is of interest when it is desired to inhibit, for instance in tobacco plants, the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-suspectible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased suspectibility to freeze injury and—because of the relatively low leaf or plant mass—attack by various diseases, especially fungus diseases. The inhibition of vegetative growth also makes closer planting possible in numerous crops, which means an increase in yield, based on the area cropped.

B. Better yields both of plant parts and plant materials may be obtained with the active ingredients according to the invention. It is thus for instance possible to induce increased formation of buds, blossom, leaves, fruit, seed grains, roots and tubers, to increase the sugar content of sugar beets, sugarcane and citrus fruit, to raise the protein content of cereals and soybeans, and to stimulate the increased formation of latex in rubber trees.

The compounds according to the invention may raise the yield by influencing plant metabolism or by promoting or inhibiting vegetative and/or generative growth.

C. Finally, it is also possible with growth regulators to shorten or lengthen growth stages and to accelerate or retard the ripening process in plant parts either before or after harvesting. A factor of economical interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of plants.

The action of the compounds according to the invention is superior to that of prior art growth regulators. This action is manifested not only in monocotyledon crops, e.g., cereals such as wheat, barley, rye, oats, rice, Indian corn or grasses, but also in dicotyledons (e.g., sunflowers, tomatoes, groundnuts, grapes, cotton, rape, and particularly, soybeans) and various ornamentals such as chrysanthemums, poinsettias and hibiscus.

The compounds according to the invention may be applied to the crop either by treating the seed, treating the soil, i.e., through the roots, or—a particularly preferred embodiment—by spraying the leaves. Because the active ingredients are well tolerated by the crop plants, application rates may vary within a wide range.

When the active ingredients are used to treat seed, active ingredient amounts of from 0.001 to 50 g, preferably from 0.01 to 10 g, per kg of seed are generally required.

When the active ingredients are applied to the soil or foliage, amounts of from 0.1 to 12 kg/ha, preferably from 0.25 to 3 kg/ha, are generally considered to be sufficient.

The compounds of the invention can be applied in conventional formulations, e.g. solutions, emulsions, suspensions, dusts, powders, pastes and granules. The form of application depends entirely on the purpose for which the agents are being used; in should, however, ensure a fine and uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g., xylene and benzene, chloroaromatics, e.g. chlorobenzene, paraffin, e.g. petroleum fractions, alcohols, e.g. methanol and butanol, amines, e.g. ethanolamine, and dimethylformamide and water; carriers, for example natural rock powders, e.g. kaolin, alumina, talc and chalk, and synthetic rock powders, e.g. kaolin, alumina, talc and chalk, and synthetic rock powders, e.g. highly disperse silica and silicates; emulsifiers and other surfactants, for example non-ionic and anionic emulsifiers, e.g. polyoxyethylene fatty alcohol ethers, alkylsulfonates and arylsulfonates, and dispersants, for example lignin, sulfite waste liquors and methylcellulose. The compounds according to the invention are preferably applied in aqueous solution, if desired together with water-miscible organic solvents, such as methanol and other lower alcohols, acetone, dimethylformamide or N-methylpyrrolidone. The formulations generally contain from 0.1 to 95, and preferably from 0.5 to 90, wt% of active ingredient.

The formulations, and the ready-to-use preparations obtained therefrom, e.g. solutions, emulsions, suspensions, powders, dusts, pastes or granules, are applied in the conventional manner, e.g. preemergence, postemergence, or as seed disinfectants.

Examples of formulations are as follows:

I. 20 parts by weight of the compound of Example 7 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

II. 3 parts by weight of the compound of Example 2 is intimately mixed with 97 parts by weight of particulate kaolin. A dust is obtained containing 3% by weight of the active ingredient.

III. 30 parts by weight of the compound of Example 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

IV. 40 parts by weight of the compound of Example 3 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04wt% of active ingredient.

V. 20 parts of the compound of Example 4 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

VI. 90 parts by weight of the compound of Example 1 is mixed with 10 parts by weight of N-methyl-α-pyrrolidone. A mixture is obtained which is suitable for application in the form of very fine drops.

VII. 20 parts by weight of the compound of Example 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

VIII. 20 parts by weight of the compound of Example 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IX. 10 parts by weight of the compound of Example 10, 20 parts by weight of polyoxyethylene sorbitan monolaurate (Tween 20 ®), 20 parts by weight of methanol and 50 parts by weight of water are stirred to give a solution containing 10 wt% of the active ingredient. More dilute solutions may be prepared by adding water.

The agents according to the invention may, in these application forms, also be mixed and applied with other active ingredients, e.g., herbicides, insecticides, other growth regulators, fungicides and fertilizers. When mixed with other growth regulators, the spectrum of action is in many cases increased; with a number of these compositions, synergistic effects also occur; i.e., the action of the combination product is greater than the effect of the individual components added together.

Examples of fungicides which may be combined with the compounds according to the invention are dithiocarbamates and derivatives thereof, such as:
Ferric dimethyldithiocarbamate,
zinc dimethyldithiocarbamate,
manganese ethylenebisdithiocarbamate,
zinc ethylenebisthiocarbamate,
tetramethylthiuram disulfide,
manganese-zinc ethylenediamine-bisdithiocarbamate,
zinc—(,N,N'-propylene-bisdithiocarbamate),
ammonia complex of zinc—(N,N'-ethylene)-bisdithiocarbamate,
and
N,N'-polyethylene-bis-(thiocarbamoyl)-disulfide,
ammonia complex of zinc-(N,N'-propylene-bisdithiocarbamate),
and
N,N'-polypropylene-bis-(thiocarbamoyl)-disulfide,
nitrophenol derivatives, such as dinitro-(1-methylheptyl)-phenylcrotonate
2-sec-butyl-4,6-dinitrophenyl-3,5-dimethylacrylate,
2-sec-butyl-4,6-dinitrophenylisopropylcarbonate,
heterocyclic structures, such as:
N-trichloromethylthiotetrahydrophthalimide,
N-trichloromethylthiophthalimide,
2-heptadecyl-2-imidazoline acetate,
2,4-dichloro-6-(o-chloroanilino)-s-triazine,
O,O-diethylphthalimidophosphorothionate,
5-amino-1-[bis-(dimethylamino)-phosphynyl]-3-phenyl-1,2,4-triazole,
5-ethoxy-3-trichloromethyl-1,2,4-thiadiazole,
2,3-dicyano-1,4-dithiaanthraquinone,
2-thio-1,3-dithio-(4,5-b)-quinoxaline,
methyl-1-(butylcarbamoyl)-2-benzimidazole carbamate,
2-methoxycarbonylaminobenzimidazole,
2-thiocyanomethylthiobenzothiazole,
4-(2-chlorophenylhydrazono)-3-methyl-5-isooxazolone,
pyridine-2-thiol-1-oxide,
8-hydroxyquinoline and its copper salt,
2,3-dihydro-5-carboxanilido-6-methyl-1,4-oxathiin-4,4-dioxide,
2,3-dihydro-5-carboxanilido-6-methyl-1,4-oxathiin,
2-[furyl-(2)]-benzimidazole,
piperazine-1,4-diyl-bis[1-(2,2,2-trichloroethyl)-formamide],
2-[thiazolyl-(4)]-benzimidazole,
5-butyl-2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl)-2-thioureido)-benzene,
and various fungicides, such as:
dodecylguanidine acetate
3-[2-(3,5-dimethyl-2-oxycyclohexyl)-2-hydroxyethyl]-glutarimide hexachlorobenzene,
N-dichlorofluoromethylthio-N,N'-dimethyl-N-phenylsulfuric acid diamide,
N-dichlorofluoromethylthio-N-methyl-N'-methyl-N-phenylsulfuric acid diamide,
D,L-methyl-N-(2,6-dimethylphenyl)-N-fur-2-yl-alanate, methyl D,L-N-(2,6-dimethylphenyl)-N-(2'-methoxyacetyl)-alanate,
diisopropyl 5-nitroisophthalate,
2,5-dimethylfuran-3-carboxylic acid anilide,
2,5-dimethylfuran-3-carboxylic acid cyclohexylamide,
2-methylbenzoic acid anilide,
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
2,3-dichloro-1,4-naphthoquinone,
1,4-dichloro-2,5-dimethoxybenzene,
p-dimethylaminobenzene diazosodium sulfonate,
1-chloro-2-nitropropane,
polychloronitrobenzenes such as pentachloronitrobenzene methyl isocyanate
fungicidal antibiotics, e.g., griseofulvin and kasugamycin tetrafluorodichloroacetone,
1-phenylthiosemicarbazide,
Bordeaux mixture
nickel-containing compounds, and sulfur.

The following examples demonstrate the action of the compounds according to the invention as growth regulators; however, further applications as growth regulators are not excluded.

Greenhouse experiment

Plastic pots approx. 12.5 cm in diameter were filled with a peat culture substrate provided with sufficient nutrients, and test plants grown therein. In the post-emergence treatment, the substances to be tested were sprayed, as aqueous formulations at various concentrations, onto the plants. The growth-regulating action observed was confirmed at the end of the experiment by height measurement. The values obtained were compared with those for untreated plants. In these experiments, which were carried out in spring barley, lawn and spring rape, particularly the substances of Examples 1, 2, 4, 5, 7, 12, 15, 18, 19, 25, 33, 35 and 50 exhibited a better action than the comparative compounds chlorocholine chloride (ccc) and 3,3-dimethyl-2-(1,2,4-triazol-1-(4-chlorobenzoyl)-butane.

The reduction in growth height was accompanied by an intenser coloring of the leaves. The increased chlorophyll content is indicative of an increased rate of photosynthesis, so that a higher yield may be expected.

We claim:

1. A 1,3-dioxan-5-yl-alkenyltriazole of the formula

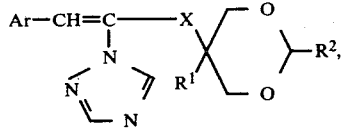

where $R^1$ and $R^2$ are identical or different and each is hydrogen or alkyl of 1 to 5 carbon atoms, Ar is furanyl, thienyl, biphenylyl or naphthyl, or is phenyl which is unsubstituted or substituted by alkyl, alkoxy or alkenyl, each of 1 to 5 carbon atoms, or by fluorine, chlorine, bromine, iodine, nitro, trifluoromethyl or phenoxy, and X is C═O, —CH(OH)— or —CH(O—COR$^3$)—, where $R^3$ is unsubstituted or halogen- or alkoxy-substituted alkyl of 1 to 5 carbon atoms or alkenyl of 2 to 5 carbon atoms or aryl, and its salts and metal complexes.

2. A 1,3-dioxan-5-yl-alkenyltriazole as defined in claim 1, which is 1-(2-ethyl-5-methyl-1,3-dioxan-5-yl)-2-(1,2,4-triazol-1-yl)-3-(naphth-1-yl)-propen-1-ol, 1-(2-ethyl-5-methyl-1,3-dioxan-5-yl)-2-(1,2,4-triazol-1-yl)-3-(4-chlorophenyl)-propen-1-one, 1-(2-ethyl-5-methyl-1,3-dioxan-5-yl)-2-(1,2,4-triazol-1-yl)-3-(4-chlorophenyl)-propen-1-ol, 1-(5-methyl-1,3-dioxan-5-yl)-2-(1,2,4-triazol-1-yl)-3-(4-bromophenyl)-propen-1-one, 1-(5-methyl-1,3-dioxan-5-yl)-1-acetoxy-2-(1,2,4-triazol-1-yl)-3-(4-bromophenyl)-prop-2-ene, 1-(2-ethyl-5-methyl-1,3-dioxan-5-yl)-2-(1,2,4-triazol-1-yl)-3-(4-bromophenyl)-propen-1-one, 1-(2-ethyl-5-methyl-1,3-dioxan-5-yl)-2-(1,2,4-triazol-1-yl)-3-(4-bromophenyl)-propen-1-ol, 1-(5-methyl-1,3-dioxan-5-yl)-2-(1,2,4-triazol-1-yl)-3-(4-trifluoromethylphenyl)-propen-1-ol, 1-(5-methyl-1,3-dioxan-5-yl)-2-(1,2,4-triazol-1-yl)-3-(4-methylphenyl)-propen-1-one, and 1-(5-methyl-1,3-dioxan-5-yl)-2-(1,2,4-triazol-1-yl)-3-(4-methylphenyl)-propen-1-ol.

3. A composition for regulating plant growth, comprising an effective amount of one or more compounds as defined in claim 1 and a solid or liquid carrier.

4. A process for regulating plant growth which comprises applying to the plants or their habitat an effective growth regulating amount of one or more of the compounds defined in claim 1.

5. The composition defined in claim 3 which further includes at least one surfactant.

6. A compound of the formula I as defined in claim 1 wherein Ar is 4-chlorophenyl, 4-bromophenyl or 4-methylphenyl.

7. A compound of the formula I as defined in claim 6 wherein X is C═O.

8. A compound of the formula I as defined in claim 7 wherein $R^1$ is methyl.

9. A compound of the formula as defined in claim 8 wherein $R^2$ is ethyl.

10. A compound of the formula I as defined in claim 1 which is 1-(5-methyl-1,3-dioxan-5-yl)-2-(1,2,4-triazol-1-yl)-3-(4-bromophenyl)-propen-1-ol.

* * * * *